(12) United States Patent
Alavi et al.

(10) Patent No.: US 12,241,798 B2
(45) Date of Patent: Mar. 4, 2025

(54) SELF-AWARE COMPOSITE MECHANICAL METAMATERIALS AND METHOD FOR MAKING SAME

(71) Applicant: UNIVERSITY OF PITTSBURGH—OF THE COMMONWEALTH SYSTEM OF HIGHER EDUCATION, Pittsburgh, PA (US)

(72) Inventors: Amir Alavi, Pittsburgh, PA (US); Kaveh BarRI, Pittsburgh, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 749 days.

(21) Appl. No.: 17/369,640

(22) Filed: Jul. 7, 2021

(65) Prior Publication Data

US 2022/0011176 A1 Jan. 13, 2022

Related U.S. Application Data

(60) Provisional application No. 63/048,943, filed on Jul. 7, 2020.

(51) Int. Cl.
 *G01L 1/00* (2006.01)
 *H02N 2/18* (2006.01)
 *A61B 5/00* (2006.01)
 *A61B 5/0215* (2006.01)
(52) U.S. Cl.
 CPC ............ *G01L 1/005* (2013.01); *H02N 2/186* (2013.01); *A61B 5/0215* (2013.01); *A61B 5/6862* (2013.01)

(58) Field of Classification Search
 CPC ....... G01L 1/005; H02N 2/186; A61B 5/0215; A61B 5/6862; B33Y 80/00
 See application file for complete search history.

(56) References Cited

U.S. PATENT DOCUMENTS

| | | | | |
|---|---|---|---|---|
| 7,750,869 B2* | 7/2010 | Mosallaei | .......... | H01Q 15/0086 343/787 |
| 8,125,717 B2* | 2/2012 | Sanada | .............. | H01Q 15/0086 359/315 |
| 11,498,282 B1* | 11/2022 | Walsh | ..................... | B33Y 10/00 |
| 11,686,638 B2* | 6/2023 | Farhangdoust | ......... | G01L 9/008 73/721 |
| 11,700,773 B2* | 7/2023 | Farhangdoust | ........ | H10N 30/88 |
| 2022/0206089 A1* | 6/2022 | Zhao | .................. | G01R 33/3642 |
| 2022/0209686 A1* | 6/2022 | Alavi | ....................... | H02N 1/04 |
| 2023/0325614 A1* | 10/2023 | Alavi | ..................... | G11C 23/00 703/6 |

* cited by examiner

*Primary Examiner* — Freddie Kirkland, III
(74) *Attorney, Agent, or Firm* — Paul D. Bangor, Jr., Esq.; Clark Hill PLC

(57) ABSTRACT

A self-aware composite mechanical metamaterial, comprising first and second electrically conductive components disposed relative to each other to act as opposite electrodes to induce contact electrification; wherein the first and second electrically conductive components, along with a dielectric component serving as a skeleton of the self-aware composite mechanical metamaterial, form a lattice of snapping curved semicircular-shaped segments, wherein each of the snapping curved semicircular-shaped segments has an elastic snap-through instability mechanism; and wherein the lattice comprises periodic repeatable parallel rows of the snapping curved semicircular-shaped segments.

20 Claims, 12 Drawing Sheets

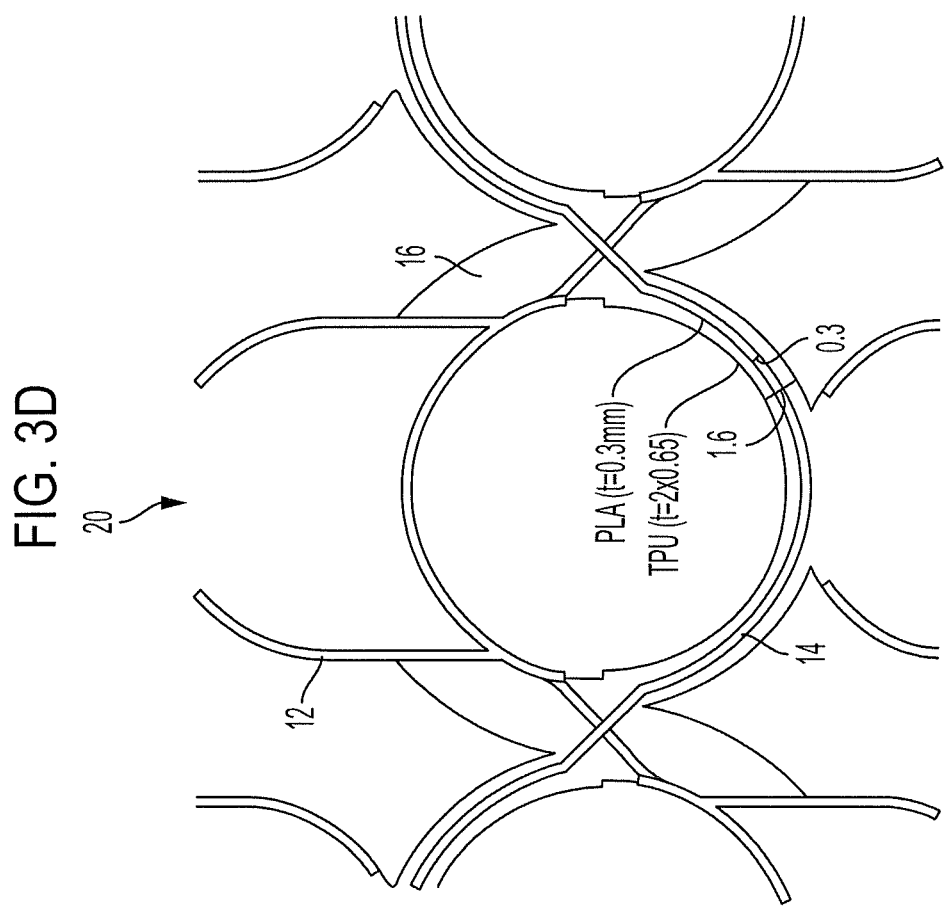

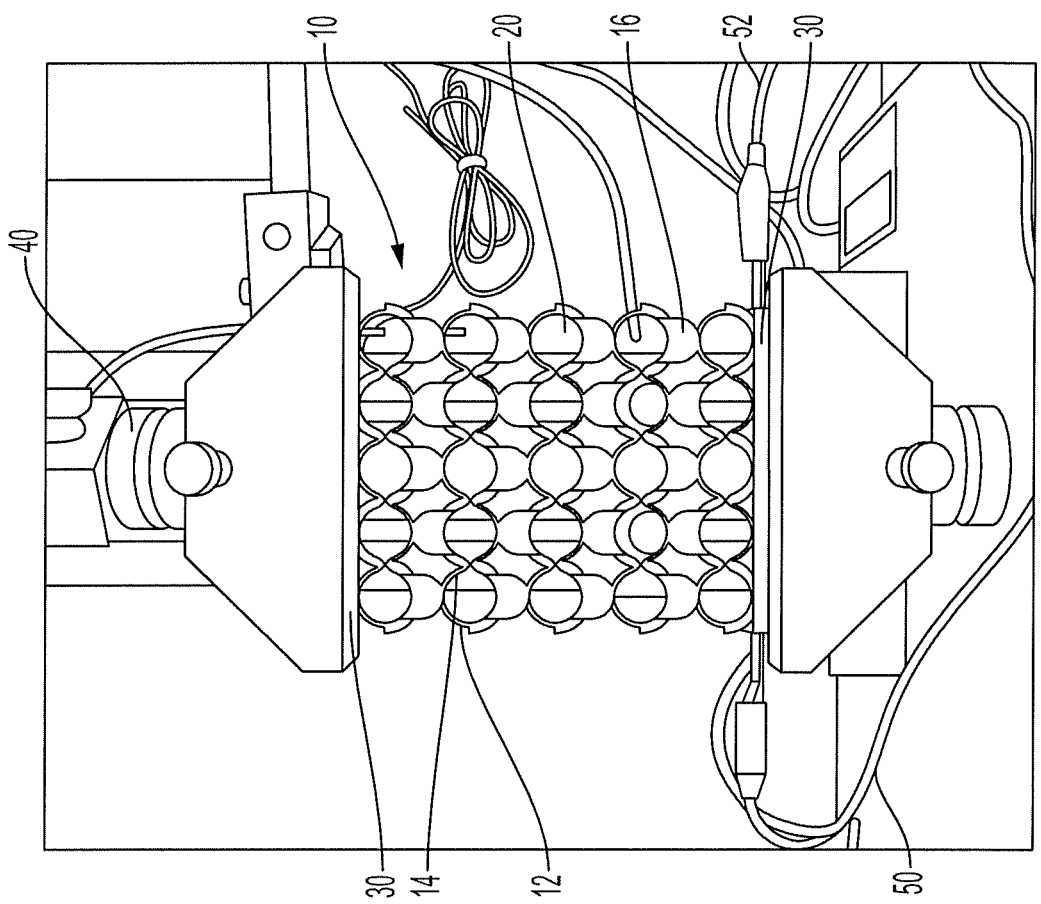

SELF-AWARE COMPOSITE MECHANICAL METAMATERIALS AND METHOD FOR MAKING SAME

RELATED APPLICATION

This application claims priority benefit under 35 U.S.C. § 119(e) of U.S. Provisional Application No. 63/048,943 filed Jul. 7, 2020 the contents of which are herein incorporated by reference.

FIELD OF THE DISCLOSURE

Technical Field

The present disclosure generally relates to the field of mechanical metamaterials and methods.

Background

The next generation of materials preferably will be adaptive, multifunctional and tunable. This goal can be achieved by metamaterials that enable development of advanced artificial materials with novel functionalities. During the last few years, the emerging concept of structure-dominated mechanical metamaterials (MMs) has received increasing attention. MMs gain their tailored unprecedented/counter-intuitive mechanical properties from their rationally-designed structures rather than inheriting them directly from their chemical composition. The main reason for developing MMs is to engineer materials with unique properties that are not found in naturally occurring materials. Additive manufacturing has been a major driving force in the exploration of MMs since virtually any topology can be obtained to probe the vast design space created by geometric changes in the material structure. However, a substantial portion of the current effort in the arena of MMs has been merely going into exploring new geometrical design of micro/nano-architectures to improve or identify unusual sets of mechanical properties. Currently, there is a critical shortage in research needed to engineer new aspects of intelligence into the texture of mechanical metamaterials for multifunctional applications. In this context, the next stage of this technological revolution is development of self-aware MMs that can sense, empower and program themselves. To address this challenge, the present disclosure introduces a new class of multifunctional MMs that offers new sensing and energy harvesting functionalities in addition to the enhanced mechanical properties of "classical MMs".

BRIEF SUMMARY OF THE DISCLOSURE

In a preferred aspect, the present disclosure comprises a self-aware composite mechanical metamaterial, comprising: first and second electrically conductive components disposed relative to each other to act as opposite electrodes to induce contact electrification; wherein the first and second electrically conductive components, along with a dielectric component serving as a skeleton of the self-aware composite mechanical metamaterial, form a lattice of snapping curved semicircular-shaped segments, wherein each of the snapping curved semicircular-shaped segments has an elastic snap-through instability mechanism; and wherein the lattice comprises periodic repeatable parallel rows of the snapping curved semicircular-shaped segments.

In another preferred aspect of a self-aware composite mechanical metamaterial of the present disclosure, the first and second electrically conductive components are embedded in the dielectric component.

In yet another preferred aspect of a self-aware composite mechanical metamaterial of the present disclosure, a structure of the self-aware composite mechanical metamaterial forms a composite matrix of the electrically conductive and dielectric components in a periodic manner.

In another preferred aspect of a self-aware composite mechanical metamaterial of the present disclosure, each of the snapping curved semicircular-shaped segments comprises a portion of each of the first electrically conductive component, the second electrically conductive component and the dielectric component.

In yet another preferred aspect of a self-aware composite mechanical metamaterial of the present disclosure, opposing, parallel ends of the lattice are bound to respective supporting members.

In another preferred aspect of a self-aware composite mechanical metamaterial of the present disclosure, the lattice comprises a 5 by 5 array of the snapping curved semicircular-shaped segments.

In another preferred aspect of a self-aware composite mechanical metamaterial of the present disclosure, the electrically conductive components comprise polylactic acid.

In a further preferred aspect of a self-aware composite mechanical metamaterial of the present disclosure, the electrically conductive components comprise carbon black.

In another preferred aspect of a self-aware composite mechanical metamaterial of the present disclosure, the electrically conductive components comprise polylactic acid and carbon black.

In a further preferred aspect of a self-aware composite mechanical metamaterial of the present disclosure, the dielectric component comprises polyurethane.

In another preferred aspect of a self-aware composite mechanical metamaterial of the present disclosure, the electrically conductive components comprise polylactic acid and carbon black and the dielectric component comprises polyurethane.

In another preferred aspect, the present disclosure comprises a method of manufacturing a self-aware composite mechanical metamaterial comprising first and second electrically conductive components disposed relative to each other to act as opposite electrodes to induce contact electrification; wherein the first and second electrically conductive components, along with a dielectric component serving as a skeleton of the self-aware composite mechanical metamaterial, form a lattice of snapping curved semicircular-shaped segments, wherein each of the snapping curved semicircular-shaped segments has an elastic snap-through instability mechanism; and wherein the lattice comprises periodic repeatable parallel rows of the snapping curved semicircular-shaped segments, comprising using 3D printing or other additive manufacturing process employing multi-material filaments to produce the lattice comprising periodic repeatable parallel rows of the snapping curved semicircular-shaped segments.

In yet another preferred aspect, the present disclosure comprises an energy harvester comprising a self-aware composite mechanical metamaterial, comprising first and second electrically conductive components disposed relative to each other to act as opposite electrodes to induce contact electrification; wherein the first and second electrically conductive components, along with a dielectric component serving as a skeleton of the self-aware composite mechanical metamaterial, form a lattice of snapping curved semicircular-shaped segments, wherein each of the snapping curved semicircular-shaped segments has an elastic snap-through instability mechanism; and wherein the lattice comprises periodic repeatable parallel rows of the snapping curved semicircular-shaped segments.

In yet a further preferred aspect, the present disclosure comprises a sensor comprising a self-aware composite mechanical metamaterial, comprising first and second electrically conductive components disposed relative to each other to act as opposite electrodes to induce contact electrification; wherein the first and second electrically conductive components, along with a dielectric component serving as a skeleton of the self-aware composite mechanical metamaterial, form a lattice of snapping curved semicircular-shaped segments, wherein each of the snapping curved semicircular-shaped segments has an elastic snap-through instability mechanism; and wherein the lattice comprises periodic repeatable parallel rows of the snapping curved semicircular-shaped segments.

BRIEF DESCRIPTION OF THE DRAWINGS

For the present disclosure to be easily understood and readily practiced, the present disclosure will now be described for purposes of illustration and not limitation in connection with the following figures, wherein:

FIG. 1 shows in (a) a preferred composition of a "self-aware composite mechanical metamaterial" (SCMM) system of the present disclosure; FIG. 1 shows in (b) a preferred flying wing aircraft with self-diagnostic and energy harvesting wings made of a network of SCMM structures; and FIG. 1 shows in (c) a preferred self-powered and self-sensing cardiovascular stent using a preferred SCMM of the present disclosure for continuous monitoring of the artery radial pressure changes due to tissue overgrowth;

FIG. 3D shows the geometry of a preferred unit cell composed of the conductive layers and dielectric layers that are involved in the contact-separation process of a preferred 2D MM with parallel semicircular-shaped snapping segments of the present disclosure;

FIG. 4A shows a preferred self-sensing and self-charging 2D SCMM of the present disclosure with a 5×5 array of unit cells 20;

DETAILED DESCRIPTION OF PREFERRED EMBODIMENTS

In the following detailed description, reference is made to the accompanying examples and figures that form a part hereof, and in which is shown, by way of illustration, specific embodiments in which the inventive subject matter may be practiced. These embodiments are described in sufficient detail to enable those skilled in the art to practice them, and it is to be understood that other embodiments may be utilized and that structural or logical changes may be made without departing from the scope of the inventive subject matter. Such embodiments of the inventive subject matter may be referred to, individually and/or collectively, herein by the term "disclosure" merely for convenience and without intending to voluntarily limit the scope of this application to any single inventive concept if more than one is in fact disclosed.

The following description is, therefore, not to be taken in a limited sense, and the scope of the inventive subject matter is defined by the appended claims and their equivalents.

Figure 1:
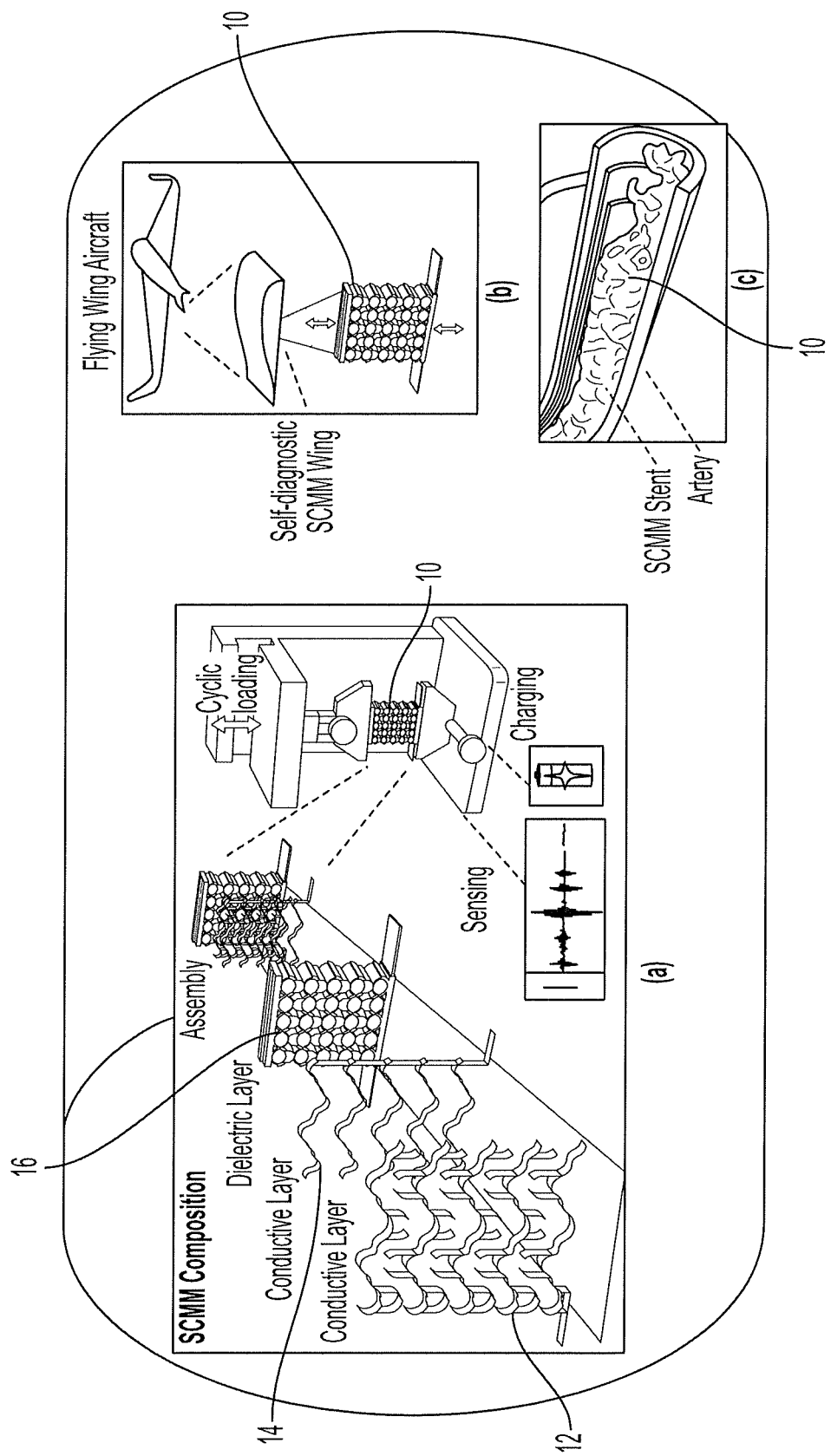
FIG. 1 shows visions of the proposed multifunctional MM concept of the present disclosure for active sensing and energy harvesting.
Figure 2:
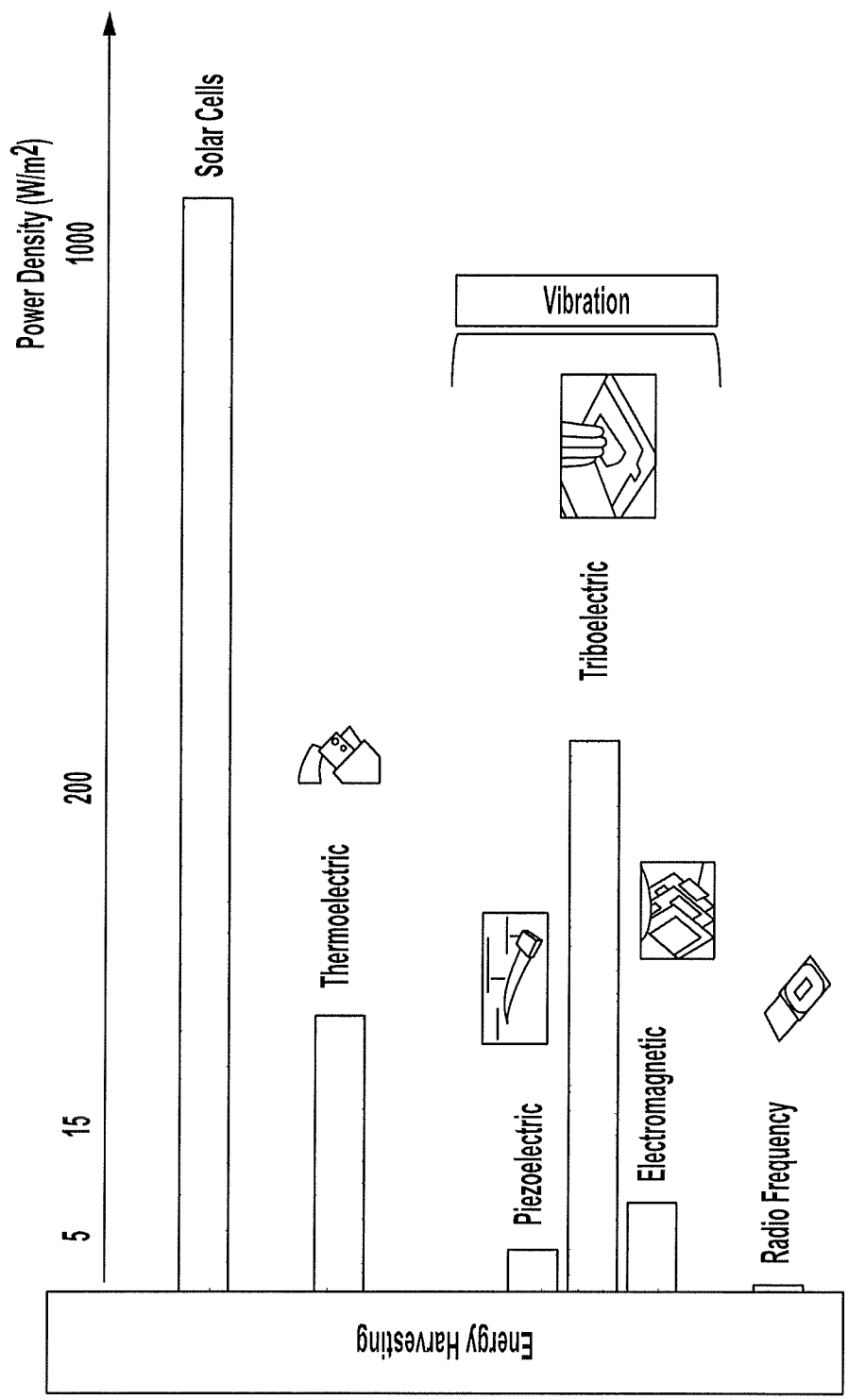
FIG. 2 shows power density for different available energy harvesting modalities.

The present disclosure is directed to a new generation of composite MMs called "self-aware composite mechanical metamaterial (SCMM)" with complex internal structures toward achieving self-sensing and self-powering functionalities along with the boosted mechanical properties. The present disclosure is based on the following: (a) finely tailored and seamlessly integrated microstructures composed of topologically different triboelectric materials can form a hybrid MM system that can both harvest the energy from the external mechanical excitations and measure various levels of the forces applied to its structure; and (b) a composite MM composed of different materials that are organized in a periodic manner will boost the mechanical properties such as strength and stiffness. The feasibility of the SCMM concept of the present disclosure has been demonstrated for designing a metamaterial structure with active sensing and energy harvesting functionalities. The results have led to the grand vision for the present disclosure (shown in FIG. 1), where architecture tailoring of materials via additive manufacturing could form a new class of multifunctional MMs for a broad range of applications. FIG. 1 shows visions of the proposed multifunctional MM concept of the present disclosure for active sensing and energy harvesting: FIG. 1 shows in (a) a preferred composition of the SCMM system 10 of the present disclosure. FIG. 1 shows in (b) a flying wing aircraft with self-diagnostic and energy harvesting wings made of a network of SCMM structures 10. FIG. 1 shows in (c) a self-powered and self-sensing cardiovascular stent using SCMM 10 for continuous monitoring of the artery radial pressure changes due to tissue overgrowth. Deformation mode of the fabricated microstructures of the present disclosure preferably are engineered through a unique design so that contact electrification will occur between the two surfaces as the SCMM structure undergoes periodic deformations due to mechanical excitations. The SCMM contacting/sliding surfaces of the present disclosure will act as conductive and dielectric layers as shown in FIG. 1 at (a). Due to the contact electrification, the conductive and dielectric layers will accumulate positive and negative charges, respectively. As the SCMM structure of the present disclosure is unloaded, the transferred charge will remain on the dielectric surface. This will form a static electric field and a potential difference between the conductive layers. By increasing the loading amplitude, more conductive and dielectric layers of the SCMM matrix of the present disclosure will get involved in the contact-separation process, which will result in generating higher electrical output. The electrical output signals can be used for active sensing of the external mechanical excitation applied to the SCMM structure of the present disclosure. On the other hand, the generated electrical energy can be harvested and stored to empower sensors and electronics at low power.

The goal of the present disclosure is to advance the knowledge and technology required to create a new class of multifunctional MMs systems that offer self-sensing, self-monitoring, and energy harvesting properties along with boosted mechanical performance due to their composite structure.

The present disclosure preferably will aid in the discovery of materials with new properties and functionalities in the fields of aerospace (morphing/deployable space structures), biomedical devices (medical implants, stents, artificial muscles), civil infrastructure and construction. From a sensing perspective, introducing the self-sensing functionality into the MM design could in theory lay the foundations for living structures that respond to their environment and self-monitor their condition. The present disclosure preferably is directed to "self-aware structures" where structural systems utilize their entire constituent components as a sensing medium to directly infer multiple types of hidden information relating to the structure. In addition to its "inferring itself" aspects, the present disclosure has numerous applications in the structural health monitoring arena. Traditional structural health monitoring approaches use dedicated sensors which often results in dense and heterogeneous sensing systems that are difficult to install and maintain in large-scale structures. On the other hand, it is not always possible embed a traditional sensor (such as a strain gauge) inside structures such as, in which cross-sectional or interlaminate failures may not be observable at the surface. Another bottleneck limiting the structural health monitoring applications is that permanent monitoring systems often require extensive maintenance as a consequence of the limited durability of traditional sensors and of the limited robustness and exposure to failures of typical structural health monitoring architectures. The present disclosure can address most of these challenges because it is a paradigm shift in technology where structure can be a sensing medium itself through a rational architectural design and choice of constituent materials. In addition to its self-sensing features, an SCMM system of the present disclosure is intrinsically sensitive to the applied stresses, and therefore, it can be implemented as a sensor in various materials or structural systems.

From an energy harvesting perspective, the present disclosure offers new concepts and mechanisms for materials and structures that utilize the energy that develops within them (strain and kinetic energy) for self-powering or local powering of sensing and actuating devices.

From a mechanical perspective, SCMMs of the present disclosure are preferably composed of different materials that are organized in a periodic manner. Therefore, SCMMs of the present disclosure not only inherit all features of classical MMs but could also offer significantly boosted mechanical properties due to their composite structure by overcoming the "rule of mixtures". In accordance with the present disclosure, mechanical properties of SCMMs are preferably predicted and tuned the to make them programmable tools for various engineering applications.

The performance of a two-dimensional (2D) snapping MMs 10 designed according to the SCMM concept of the present disclosure has been analyzed. An architected MM 10 containing parallel snapping curved (semicircular-shaped) segments 12, 14 with elastic snap-through instability mechanism was fabricated according to the present disclosure. The design of MMs with snap-through instabilities has been the focus of active research in recent years. Multi-stable/self-recovering snapping metamaterials have advantages in applications such as the development of tunable metamaterials with switchable properties. According to the present disclosure, the metamaterial was made up of multiple bi-stable unit cells 20. The unit cell 20 consisted of thick horizontal and vertical elements and a thin curved part. In order to incorporate the sensing and energy harvesting features into the metamaterial functionality of the SCMM 10 of the present disclosure, the triboelectrification phenomenon was incorporated into its architecture design. The triboelectrification phenomenon is a universally-existing phenomenon in the nature and people's living life and has been known for thousands of years. It describes a contact electrification phenomenon that a material/surface becomes electrically charged after it gets into contact with a different material/surface. The design process is shown in FIGS. 3A-3G.

Figure 3A:
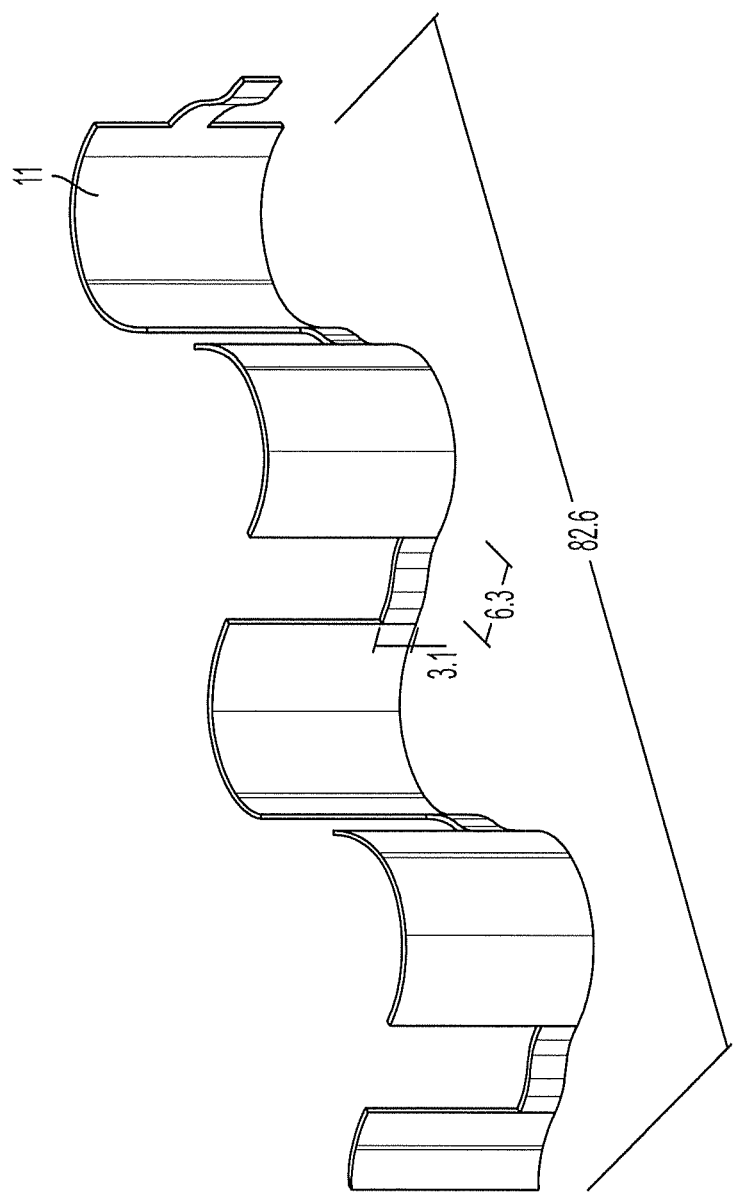
FIG. 3A shows a segment of the conductive layers of a preferred 2D MM with parallel semicircular-shaped snapping segments of the present disclosure.
Figure 3B:
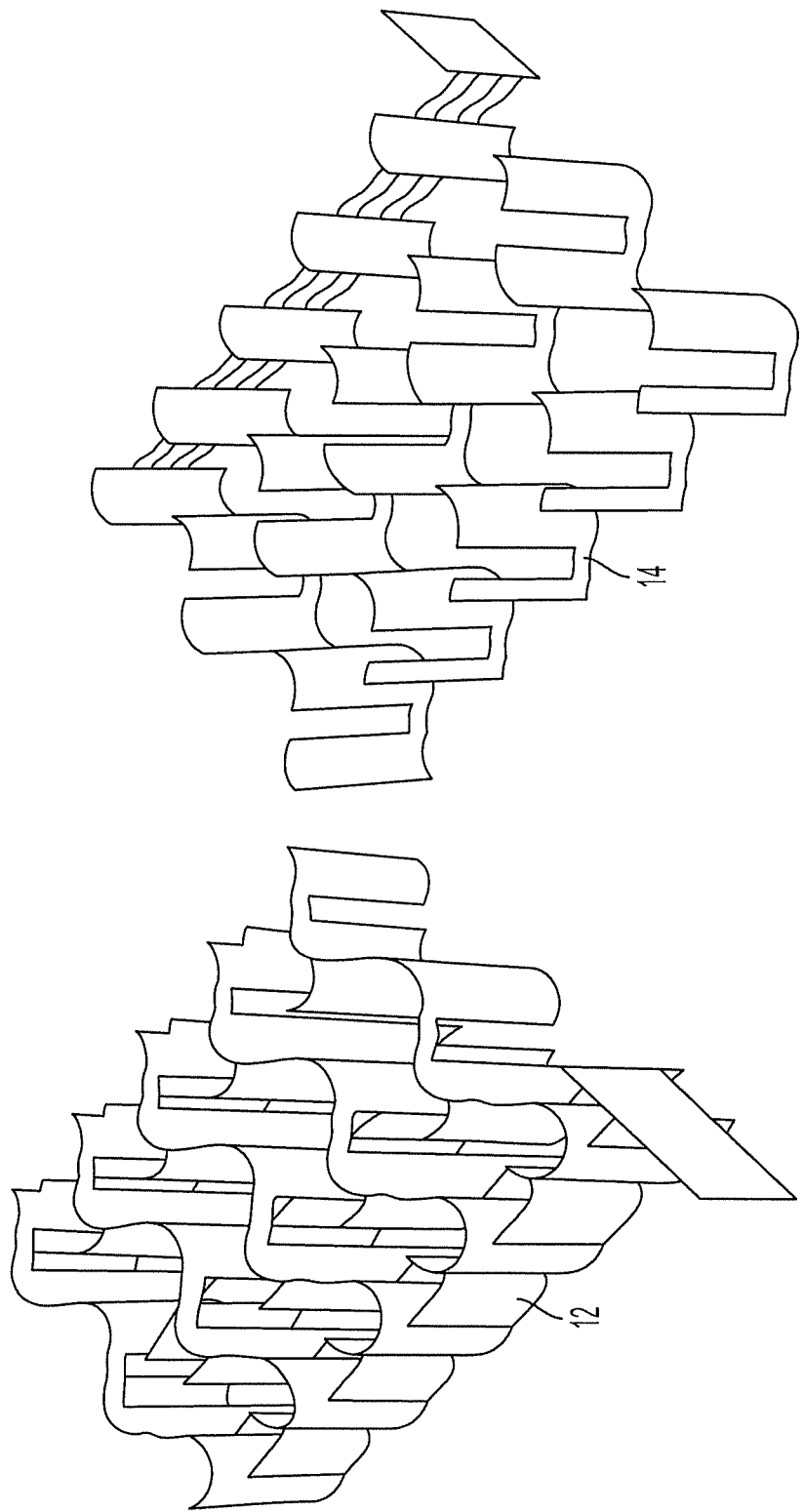
FIG. 3B shows two conductive layers created as 5 periodic repeatable segments of a preferred 2D MM with parallel semicircular-shaped snapping segments of the present disclosure.
Figure 3C:
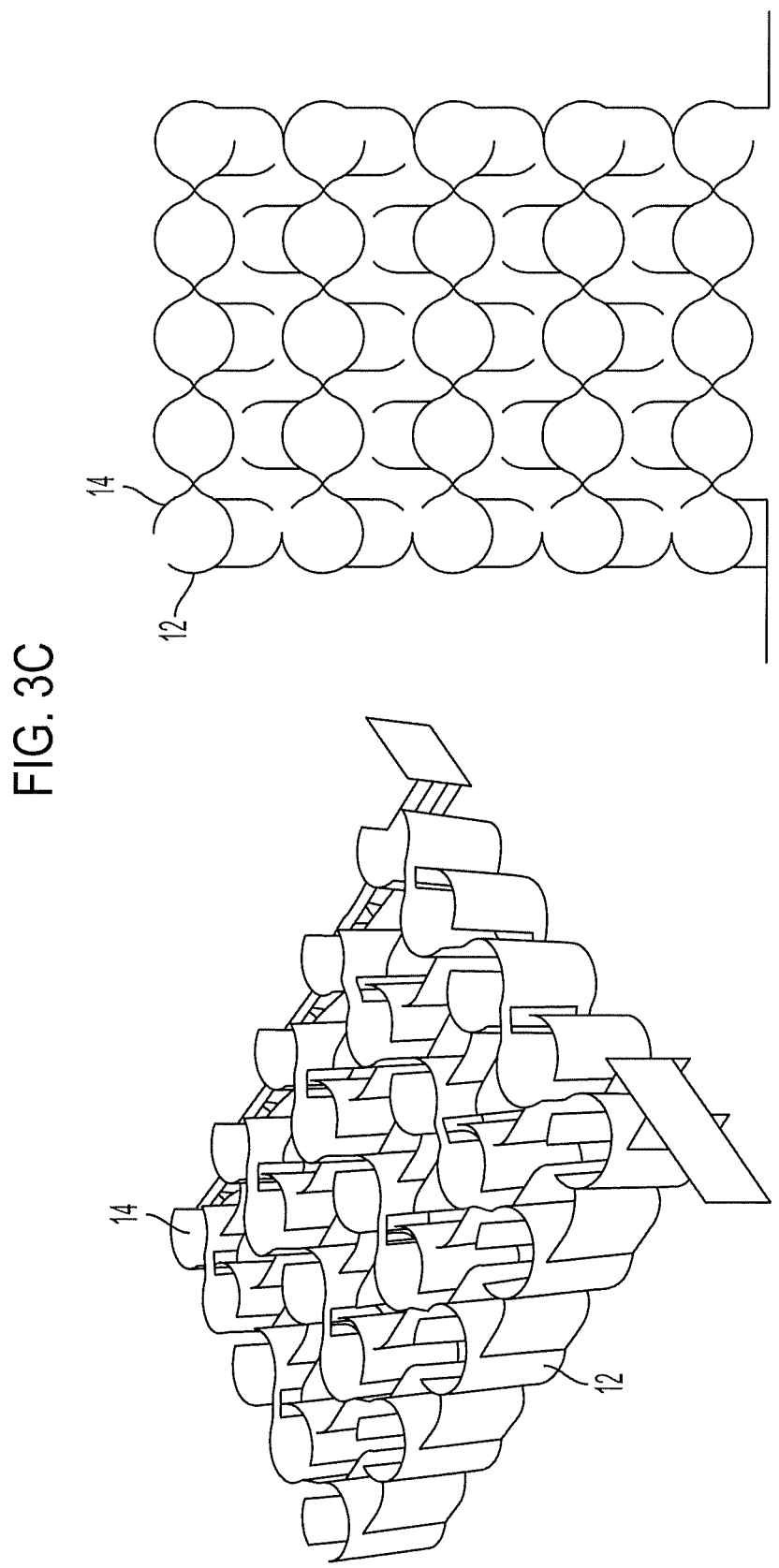
FIG. 3C shows aligned conductive layers of a preferred 2D MM with parallel semicircular-shaped snapping segments of the present disclosure.
Figure 3E:
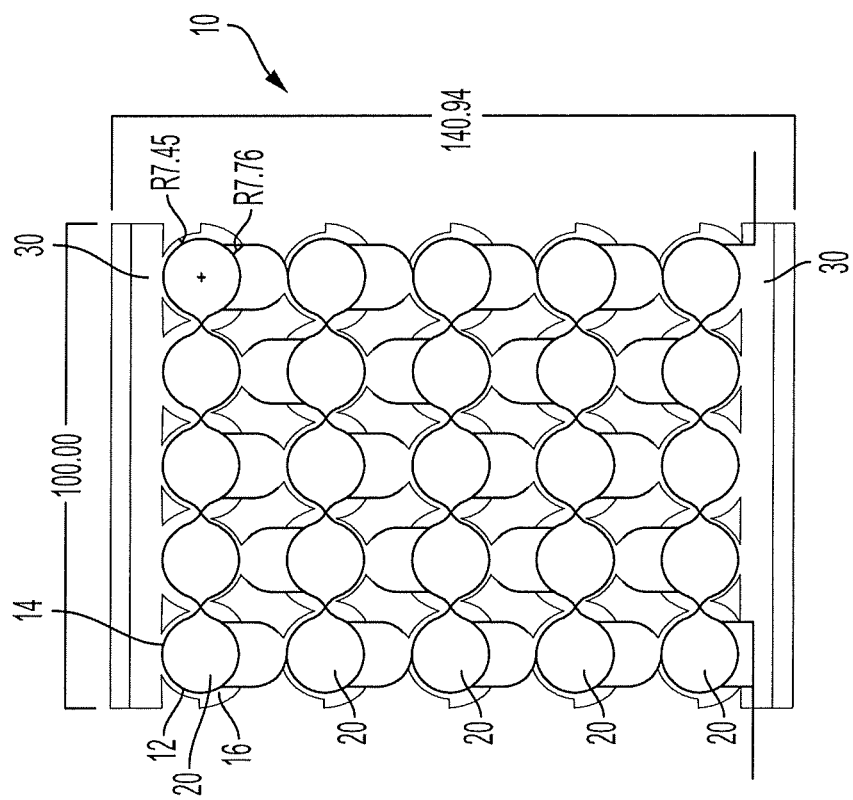
FIG. 3E and FIG. 3F show representations of the entire composite matrix of the a preferred SCCM of the present disclosure composed of two conductive layers and dielectric layers in a periodic manner in a preferred 2D MM with parallel semicircular-shaped snapping segments of the present disclosure.
Figure 3F:
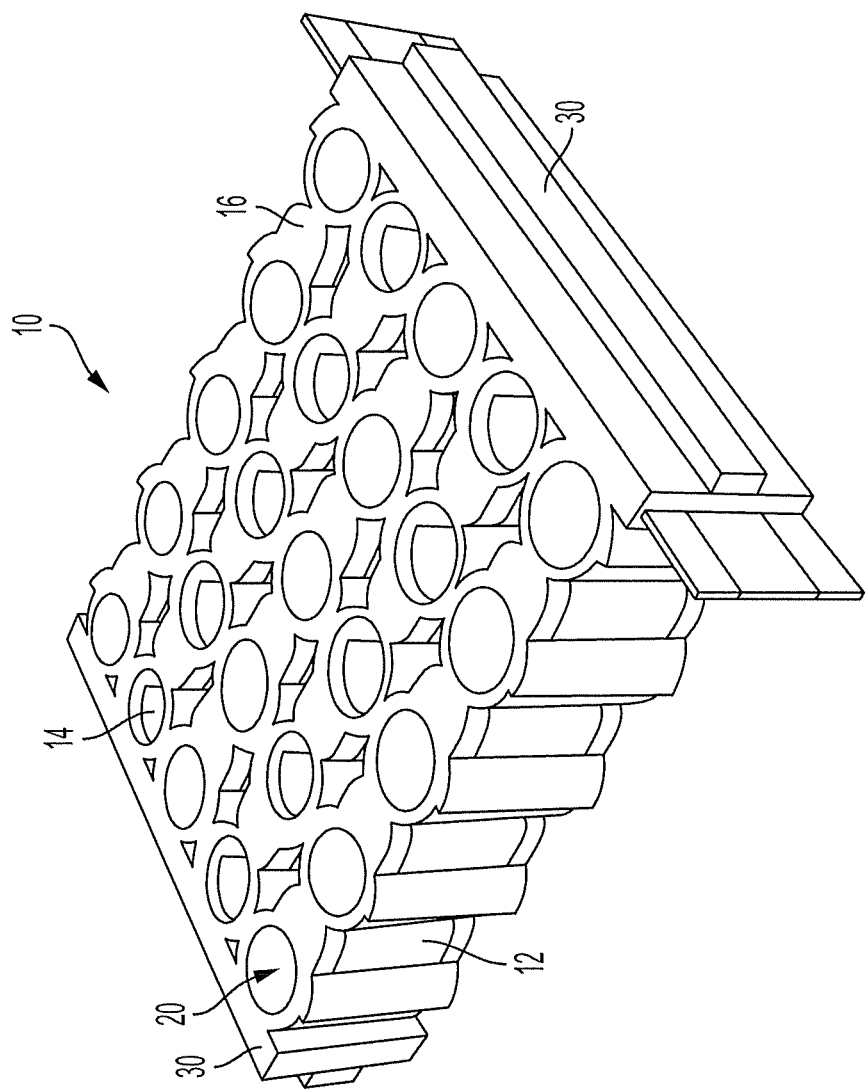
Figure 3G:
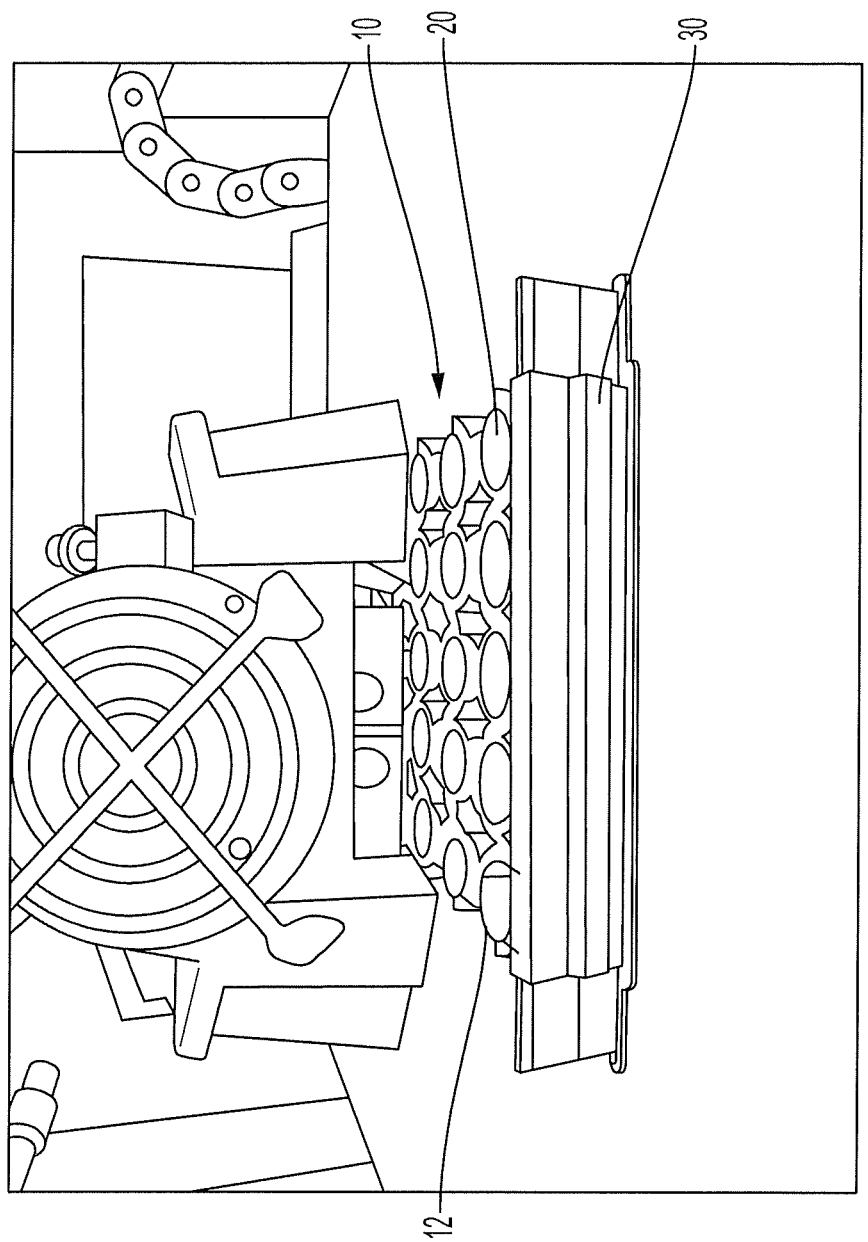
FIG. 3G shows a preferred manner of 3D printing a preferred SCCM of the present disclosure.

FIGS. 3A-3G show the designing of a 2D MM with parallel semicircular-shaped snapping segments according to the SCMM concept of the present disclosure. FIG. 3A shows a segment 11 of the conductive layers 12, 14 of a preferred 2D MM with parallel semicircular-shaped snapping segments of the present disclosure. FIG. 3B shows the two conductive layers 12, 14 created as 5 periodic repeatable segments. FIG. 3C shows aligned conductive layers 12, 14 of a preferred 2D MM with parallel semicircular-shaped snapping segments of the present disclosure. FIG. 3D shows the geometry of a symmetric unit cell 20 composed of the conductive layers 12, 14 and dielectric layers 16 that are involved in the contact-separation process of a preferred 2D MM with parallel semicircular-shaped snapping segments of the present disclosure. FIG. 3E and FIG. 3F show a schematic representation of the entire composite matrix of the SCCM 10 composed of the conductive layers 12, 14 and dielectric layers 16 in a periodic manner in a preferred 2D MM with parallel semicircular-shaped snapping segments of the present disclosure. FIG. 3G shows a preferred manner of 3D printing a SCCM 10 of the present disclosure.

In order to fabricate the 2D structure of the snapping SCMM of the present disclosure, three constituent layers were defined. The first two layers were conductive layers 12, 14 created as periodic repeatable segments 20 (FIGS. 3A-3B). The conductive layers 12, 14 were first aligned to act as opposite electrodes. Then, they were embedded inside a thicker dielectric layer 16 serving as the skeleton of the MM (FIG. 3D). As seen in FIGS. 3D-3F, the entire snapping SCMM structure 10 of the present disclosure forms composite matrix composed of the conductive layers 12, 14 and dielectric layers 16 in a periodic manner. The semicircular-shaped snapping segments include both conductive layers 12, 14 and dielectric layers 16 (FIG. 3D). The semicircular-shaped snapping segments 20 were centrally clamped by relatively thicker (stiffer) supporting segments 30 with a connection platform, as illustrated in FIGS. 3D-3E.

Preferably, the curved elements were specifically designed in mathematical/trigonometric function form to achieve smooth snap-through transition and symmetrical stable configurations before and after large deformation. In order to fabricate this complex design as one integrated unit, Raise3D Prot Dual Extruder 3D Printer was used as it supports printing with a variety of multi-material filaments. There is a wide range of organic and inorganic materials from the triboelectric series that can be used to fabricate the conductive and dielectric layers. Preferably, materials with a large difference in triboelectric polarity are used to maximize the electrification between the two layers. Polylactic Acid (PLA) with carbon black (Young's modulus E=3000 MPa, Poisson's ratio v=0.48) and Thermoplastic Polyurethane (TPU) (E=12 MPa, v=0.25) were used as the conductive and dielectric layers, respectively.

Figure 4B:
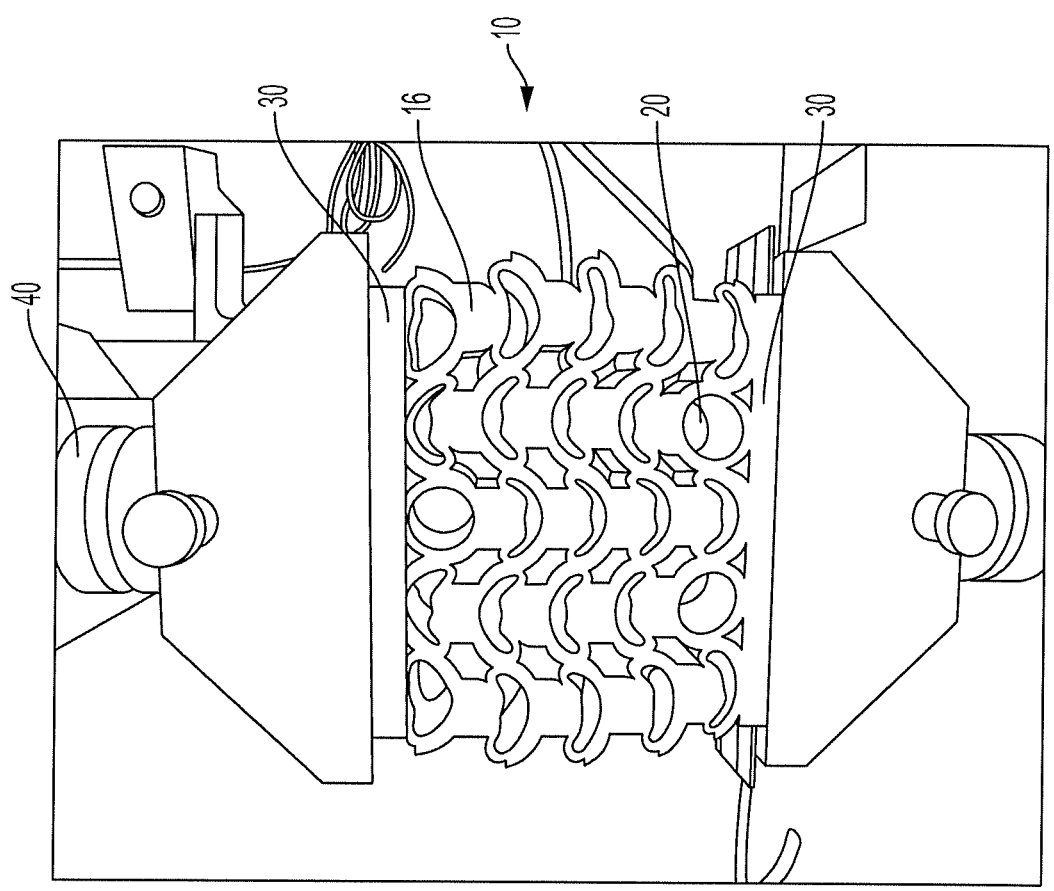
FIG. 4B shows a preferred SCCM of the present disclosure in the compacted state.

The test setup and the fabricated SCMM of the present disclosure are shown in FIG. 3G and FIGS. 4A-4B. Uniaxial loading experiments were performed on the 3D printed metamaterial specimen SCCM 10 of the present disclosure with a TestResources testing machine 40. Cycling loading at 0.5 Hz frequency was applied to the specimen SCCM 10 under displacement control until it was fully compacted. The displacement range was controlled to be between 5 mm to 10 mm. The applied load changed between 15 N and 45 N. Under uniaxial loading, the SCCM 10 undergoes a large deformation caused by stiffness mismatch between snapping (buckling instabilities) and supporting (relatively stiffer/thicker) components, exhibiting very small transverse deformation after every snapping. Based on the multi-stable/self-recovering mechanism, phase transformation/shape-reconfiguration and zero (or close to zero) Poisson's ratio can be achieved up to large morphological change (FIG. 4B).

Figure 4C:
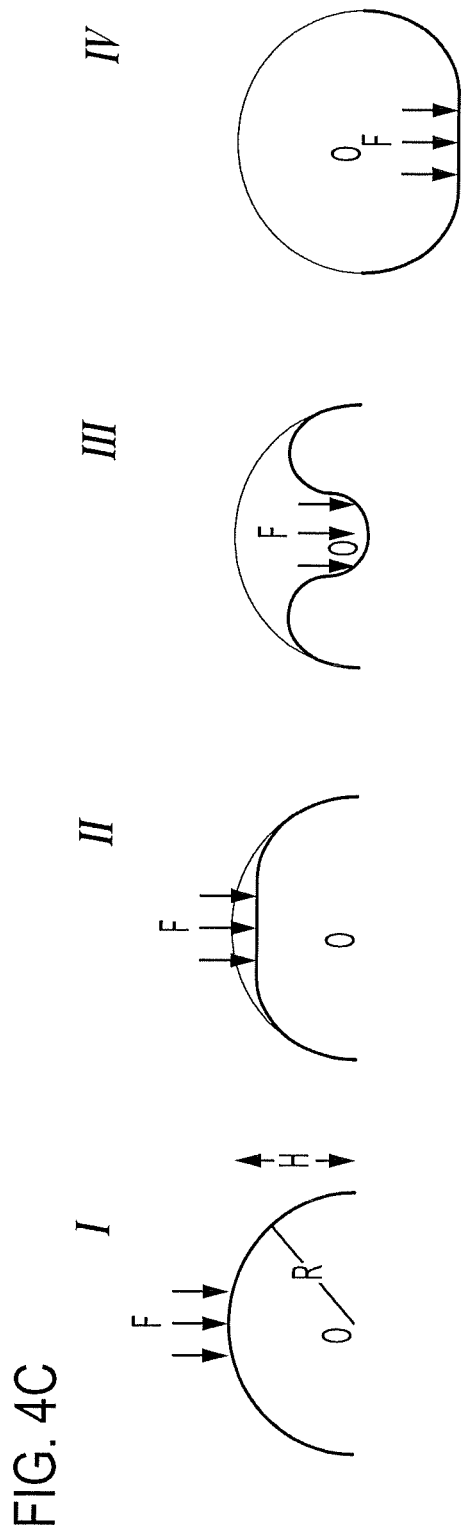
FIG. 4C shows preferred snapping mechanisms of elastic bulking semicircular-shaped snapping shells of the present disclosure.
Figure 4D:
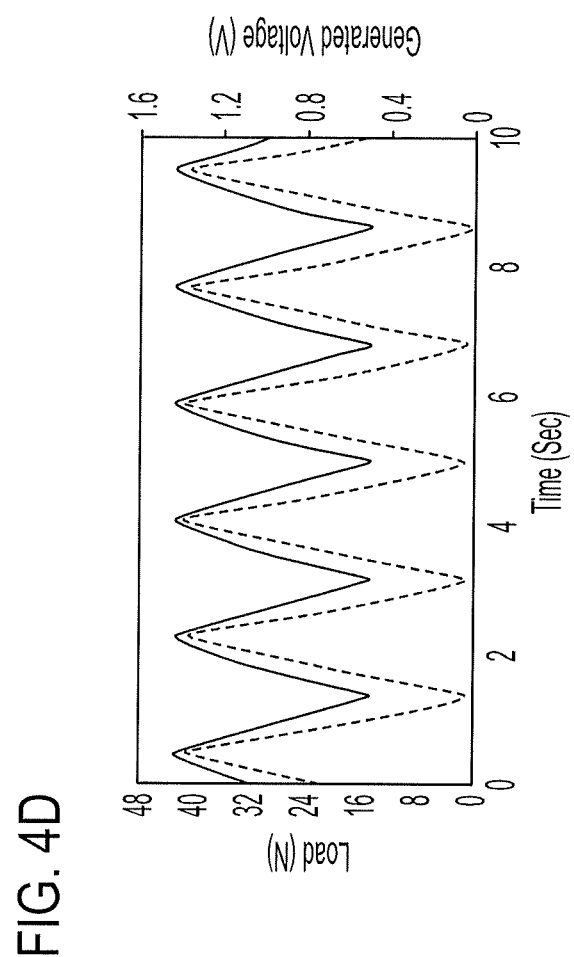
FIG. 4D shows applied cyclic loads and the corresponding voltage generated by a preferred SCCM of the present disclosure.

As shown in FIG. 4C, when a normal vertical force applied in the middle of the curved beams, the semicircular-shaped segment is mechanically deformed (buckled), snapping from first/original stable state (State I) to second/deformed stable state (State IV) at a critical applied force. In a very ideal situation, the constrained conditions at both ends are strong and the two stable states are symmetric, the reaction force will be symmetric from one to the other stable state under displacement control which means that an identical reverse force is needed that allows the deformed beams to return to their original configuration. In the case of a self-recovering snapping, the constant positive force means that the snapped segments (State IV) automatically return to their initial stable configuration (State I) after the load is removed. Under compressive loads, the SCCM 10 of the present disclosure undergoes periodic deformations and contact electrification occurs between the conductive layers 12, 14 and dielectric layers 16. By unloading the SCCM 10, a potential difference is formed between the conductive layers 12, 14. Higher loading amplitude results in larger deformations. Consequently, more conductive layers 12, 14 and dielectric layers 16 of the matrix of SCCM 10 get involved in the contact-separation process. This leads to higher rate of the electrostatically-induced electron transfer and generating higher voltage. In order to record the voltage generated due to the applied mechanical excitations, wires 50, 52 were connected to the extended parts of the conductive layers, as shown in FIG. 4A. The voltage values were read using a National Instruments 9220 DAQ module with 1 GΩ impedance. The applied cyclic loads and the corresponding voltage generated by the proposed mechanical metamaterial structure are shown in FIG. 4D. As seen, the voltage is proportional to the applied force. Also, the generated electrical energy can be readily stored using an energy harvesting circuit.

FIG. 4A shows a preferred self-sensing and self-charging 2D SCMM 10 of the present disclosure with a 5×5 array of unit cells 20. FIG. 4B shows the SCCM 10 in the compacted state. FIG. 4C shows preferred snapping mechanisms of elastic bulking semicircular-shaped snapping shells of the present disclosure. FIG. 4D shows applied cyclic loads and the corresponding voltage generated by the SCCM 10.

According to the present disclosure, it is feasible to create SCMMs 10 with sensing and energy harvesting functionalities via introducing the contact electrification into the fabrication process. Preferably, the SCMMs 10 of the present disclosure will allow for measuring the force applied to the SCMM 10 by monitoring the voltage generated therefrom. The kinetic energy harvested from the external excitations of the SCMM 10 can be stored for self-powering or empowering other sensing devices. Furthermore, the SCMMs 10 of the present disclosure allow for the creation of MMs whose mechanical and electrical response can be programmed. Preferably, the snapping mechanism or the layered design of the composite matrix of the SCMMs 10 of the present disclosure can be engineered to deform in specified order or prevent random snapping, which will result in programmed triboelectrification and mechanical behaviors. Preferably, the SCMMs 10 of the present disclosure can be applied to design a variety of programmable MMs with sensing, energy harvesting properties.

In the foregoing Detailed Description, various features are grouped together in a single embodiment to streamline the disclosure. This method of disclosure is not to be interpreted as reflecting an intention that the claimed embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A self-aware composite mechanical metamaterial, comprising:
    first and second electrically conductive components disposed relative to each other to act as opposite electrodes to induce contact electrification;
    wherein the first and second electrically conductive components, along with a dielectric component serving as a skeleton of the self-aware composite mechanical metamaterial, form a lattice of snapping curved semicircular-shaped segments, wherein each of the snapping curved semicircular-shaped segments has an elastic snap-through instability mechanism; and
    wherein the lattice comprises periodic repeatable parallel rows of the snapping curved semicircular-shaped segments.

2. The self-aware composite mechanical metamaterial of claim 1, wherein the first and second electrically conductive components are embedded in the dielectric component.

3. The self-aware composite mechanical metamaterial of claim 2, wherein the lattice comprises a 5 by 5 array of the snapping curved semicircular-shaped segments.

4. The self-aware composite mechanical metamaterial of claim 2, wherein the electrically conductive components comprise polylactic acid and carbon black and the dielectric component comprises polyurethane.

5. The self-aware composite mechanical metamaterial of claim 1, wherein a structure of the self-aware composite mechanical metamaterial forms a composite matrix of the electrically conductive and dielectric components in a periodic manner.

6. The self-aware composite mechanical metamaterial of claim 5, wherein the lattice comprises a 5 by 5 array of the snapping curved semicircular-shaped segments.

7. The self-aware composite mechanical metamaterial of claim 5, wherein the electrically conductive components comprise polylactic acid and carbon black and the dielectric component comprises polyurethane.

8. The self-aware composite mechanical metamaterial of claim 1, wherein each of the snapping curved semicircular-shaped segments comprises a portion of each of the first electrically conductive component, the second electrically conductive component and the dielectric component.

9. The self-aware composite mechanical metamaterial of claim 8, wherein the lattice comprises a 5 by 5 array of the snapping curved semicircular-shaped segments.

10. The self-aware composite mechanical metamaterial of claim 1, wherein opposing, parallel ends of the lattice are bound to respective supporting members.

11. The self-aware composite mechanical metamaterial of claim 10, wherein the lattice comprises a 5 by 5 array of the snapping curved semicircular-shaped segments.

12. The self-aware composite mechanical metamaterial of claim 1, wherein the lattice comprises a 5 by 5 array of the snapping curved semicircular-shaped segments.

13. The self-aware composite mechanical metamaterial of claim 1, wherein the electrically conductive components comprise polylactic acid.

14. The self-aware composite mechanical metamaterial of claim 1, wherein the electrically conductive components comprise carbon black.

15. The self-aware composite mechanical metamaterial of claim 1, wherein the electrically conductive components comprise polylactic acid and carbon black.

16. The self-aware composite mechanical metamaterial of claim 1, wherein the dielectric component comprises polyurethane.

17. The self-aware composite mechanical metamaterial of claim 1, wherein the electrically conductive components comprise polylactic acid and carbon black and the dielectric component comprises polyurethane.

18. An energy harvester comprising the self-aware composite mechanical metamaterial of claim 1.

19. A sensor comprising the self-aware composite mechanical metamaterial of claim 1.

20. A method of manufacturing a self-aware composite mechanical metamaterial comprising first and second electrically conductive components disposed relative to each other to act as opposite electrodes to induce contact electrification; wherein the first and second electrically conductive components, along with a dielectric component serving as a skeleton of the self-aware composite mechanical metamaterial, form a lattice of snapping curved semicircular-shaped segments, wherein each of the snapping curved semicircular-shaped segments has an elastic snap-through instability mechanism; and wherein the lattice comprises periodic repeatable parallel rows of the snapping curved semicircular-shaped segments, comprising:

using 3D printing or other additive manufacturing process employing multi-material filaments to produce the lattice comprising periodic repeatable parallel rows of the snapping curved semicircular-shaped segments.

\* \* \* \* \*

UNITED STATES PATENT AND TRADEMARK OFFICE
CERTIFICATE OF CORRECTION

| | | |
|---|---|---|
| PATENT NO. | : 12,241,798 B2 | Page 1 of 1 |
| APPLICATION NO. | : 17/369640 | |
| DATED | : March 4, 2025 | |
| INVENTOR(S) | : Alavi et al. | |

It is certified that error appears in the above-identified patent and that said Letters Patent is hereby corrected as shown below:

On the Title Page

Item (72), Inventors: after Amir Alavi, Pittsburgh, PA (US):
Delete "Kaveh BarRI, Pittsburgh, PA (US)", insert --Kaveh Barri, Pittsburgh, PA (US)--

Signed and Sealed this
Twenty-ninth Day of April, 2025

Coke Morgan Stewart
*Acting Director of the United States Patent and Trademark Office*